United States Patent
Zhou

(10) Patent No.: US 8,206,373 B2
(45) Date of Patent: Jun. 26, 2012

(54) MEDICAL DEVICE INCLUDING BRAID WITH COATED PORTION

(75) Inventor: Pu Zhou, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1022 days.

(21) Appl. No.: 12/166,079

(22) Filed: Jul. 1, 2008

(65) Prior Publication Data

US 2010/0004631 A1    Jan. 7, 2010

(51) Int. Cl.
*A61M 25/16* (2006.01)
*A61M 25/00* (2006.01)

(52) U.S. Cl. .......................... 604/527; 427/2.3
(58) Field of Classification Search .............. 604/524; 427/2.3
See application file for complete search history.

(56) References Cited

U.S. PATENT DOCUMENTS

| | | | |
|---|---|---|---|
| 4,817,613 A | 4/1989 | Jaraczewski et al. | |
| 5,569,218 A | 10/1996 | Berg | |
| 5,603,705 A | 2/1997 | Berg | |
| 5,674,208 A | 10/1997 | Berg et al. | |
| 5,680,873 A | 10/1997 | Berg et al. | |
| 5,733,248 A | 3/1998 | Adams et al. | |
| 5,853,400 A | 12/1998 | Samson | |
| 5,860,983 A | 1/1999 | Wenstrom, Jr. | |
| 5,911,715 A | 6/1999 | Berg et al. | |
| 5,951,495 A | 9/1999 | Berg et al. | |
| 5,954,651 A | 9/1999 | Berg et al. | |
| 7,112,298 B2 | 9/2006 | Kampa et al. | |
| 2005/0010194 A1 | 1/2005 | Zhou | |
| 2005/0137576 A1 | 6/2005 | Packard | |
| 2007/0088319 A1 | 4/2007 | Martone | |

FOREIGN PATENT DOCUMENTS

| | | |
|---|---|---|
| EP | 0806219 | 11/1997 |
| EP | 0 807 446 B1 * | 11/2002 |
| EP | 0807446 | 11/2002 |

* cited by examiner

*Primary Examiner* — Robert D. Harlan
(74) *Attorney, Agent, or Firm* — Seager, Tufte & Wickhem, LLC

(57) ABSTRACT

Alternative design, material, manufacturing method, and use for medical devices, such as catheters, catheter shafts and the like. An example includes a medical device, such as a catheter shaft, including an elongated tubular braid comprising a plurality of filaments and including an end portion coated with a first polymeric material having a first melting point temperature, wherein the first polymeric material attaches the braid filaments together. A second polymeric material having a second melting temperature lower than the first melting point temperature may be attached to the coated end portion of the braid. In some embodiments, the underlying a first polymeric material may reduce the tendency of the braid to flair into the second polymeric material. Other examples relate to methods of making such medical devices, such as a catheter shaft, of the like.

11 Claims, 5 Drawing Sheets

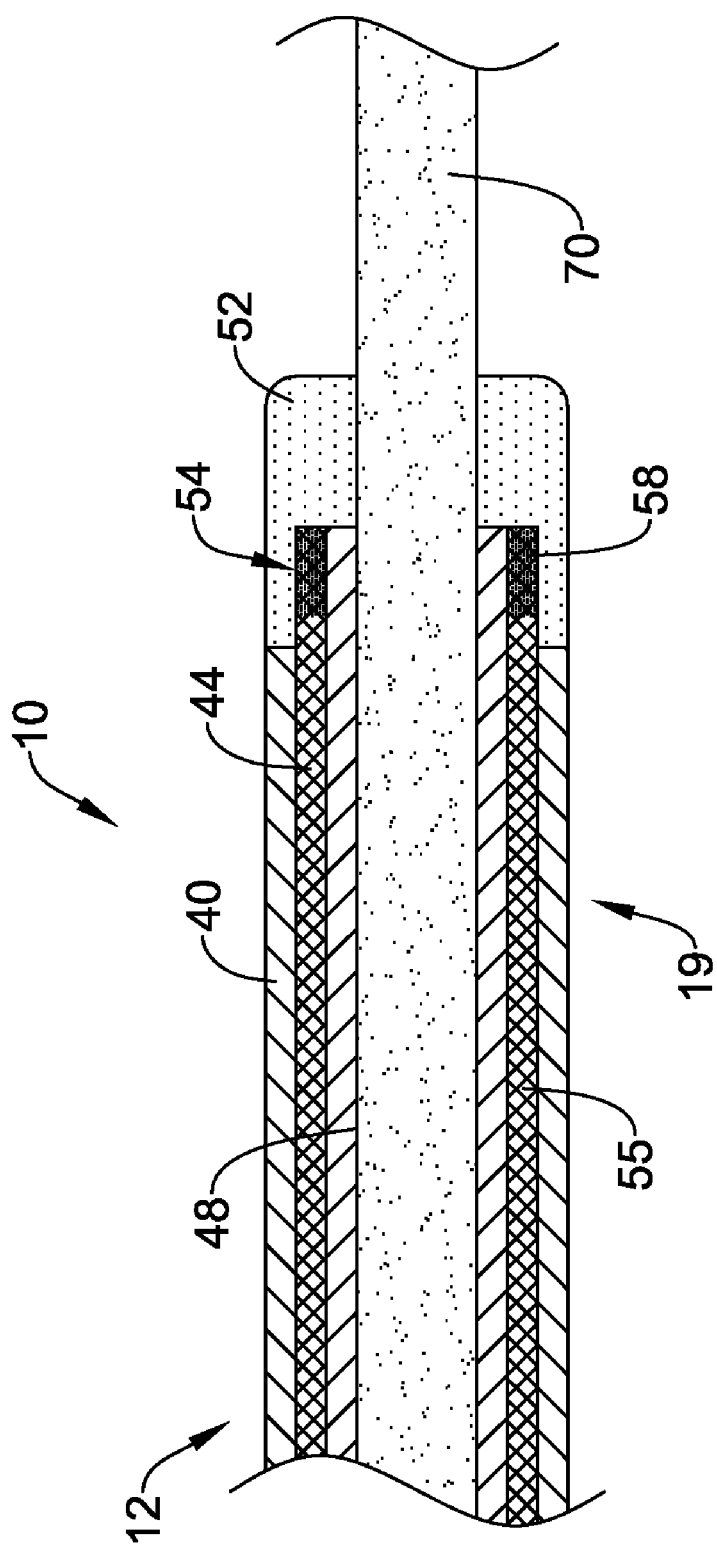

MEDICAL DEVICE INCLUDING BRAID WITH COATED PORTION

FIELD OF THE INVENTION

The invention relates to medical devices, for example, elongated medical devices for intracorpral use. More particularly, the invention relates to a medical device including a braid reinforcing member including a coated end portion and a polymer tip disposed over the coated end portion.

BACKGROUND

The use of intracorporal medical devices, such as intravascular catheters, guidewires, or the like, has become an effective method for treating many types of disease. For example, in some treatments, an intracopreal device is inserted into the anatomy, such as the vascular system, of the patient and navigated to a desired target site, and can be used in treating the target site. Using this method, many target sites in the patient's anatomy can be accessed, including the coronary, cerebral, and peripheral vasculature. Examples of therapeutic purposes for intravascular devices include percutaneous transluminal angioplasty (PTA) and percutaneous transluminal coronary angioplasty (PTCA).

Many medical devices, such as catheters, include a reinforcing structure, such as a braid, or the like, disposed within the catheter shaft. It is also generally known to provide a polymer tip member, sometimes made of a soft and/or flexible polymer, at the distal end of the catheter shaft. However, the use of a braid in combination with a soft tip material can sometimes be problematic. For example, if the end of the braid is disposed within the soft and/or flexible polymer material, the ends of the braid filaments may flair and/or migrate within the polymer material—in some cases flaring either inwardly and/or outwardly through the surface of the polymer material. As can be appreciated, such fairing can be undesirable.

The prior art offers a number of different structures and mechanisms for providing braids for medical devices. Each of these different structures and mechanisms has certain advantages and disadvantages. However, there is an ongoing need to provide alternative structures and mechanisms for medical devices, and in some cases, designs and/or methods that may aid to reduce and/or prevent the fairing of braids within such devices.

SUMMARY

The invention provides design, material, manufacturing method, and use alternatives for medical devices. For example, some embodiments relate to a medical device, such as a catheter shaft, including an elongated tubular braid comprising a plurality of filaments and including an end portion coated with a first polymeric material having a first melting point temperature, wherein the first polymeric material attaches the braid filaments together. A second polymeric material having a second melting temperature lower than the first melting point temperature may be attached to the coated end portion of the braid. In some embodiments, the underlying a first polymeric material may reduce the tendency of the braid to flair into the second polymeric material.

In some example embodiments, a shaft, such as a catheter shaft, may include elongated tubular braid comprising a plurality of braid filaments, the braid including a portion coated with a first polymeric material having a first melting point temperature such that the polymeric material connects two or more of the braid filaments together hindering them from flaring. The shaft may also include a polymer layer attached to the coated portion of the braid using a heat attachment technique, the polymer layer comprising a second polymer material having a second melting point temperature that is less than the first melting point temperature.

Some embodiments relate to a method of making a medical device, such as a catheter shaft. The method can include providing an elongate braid including a plurality of filaments and having an end portion, and providing in a liquid state a first polymeric material having a first melting point. The first polymeric material may be applied to the end portion of the braid in a liquid state, and allowed to cure to a solid state on the braid and to attach at least some of the braid filaments together. A second polymeric material may be attaches to at least the end portion of the braid, the second polymeric material having a second melting point temperature that is lower than the first melting point temperature. Attaching the second polymeric material can include heating the second polymeric material to a temperature that is below the first melting point temperature such that during the attaching of the second polymeric material, the first polymeric material remains in a solid state.

Some embodiments relate coating a tip portion of the braid with a first polymeric material having a first melting point temperature to form a coated tip portion, wherein the first polymeric material connects two or more of the braid filaments together hindering them from flaring, and attaching a layer of second polymeric material adjacent the coated tip portion through the use of an attachment technique that includes applying heat to the second polymeric material to heat it to a predetermined temperature, wherein the predetermined temperature is less than the melting point temperature of the first polymeric material.

Some embodiments relate to coating the distal tip portion of the braid with a polymeric material having a first melting point temperature to form a coated tip portion. A second polymeric material can be disposes adjacent the coated tip portion, the second polymeric material having a second melting point temperature lower than the first melting point temperature. The second polymeric material may be heated to a temperature that is at or above the second melting point temperature but below the first melting point temperature to attach the second polymeric material to the coated tip portion.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 5 longitudinal cross-sectional view of the distal portion of the catheter of FIG. 2 showing the distal tip member being attached.

Figure 1:
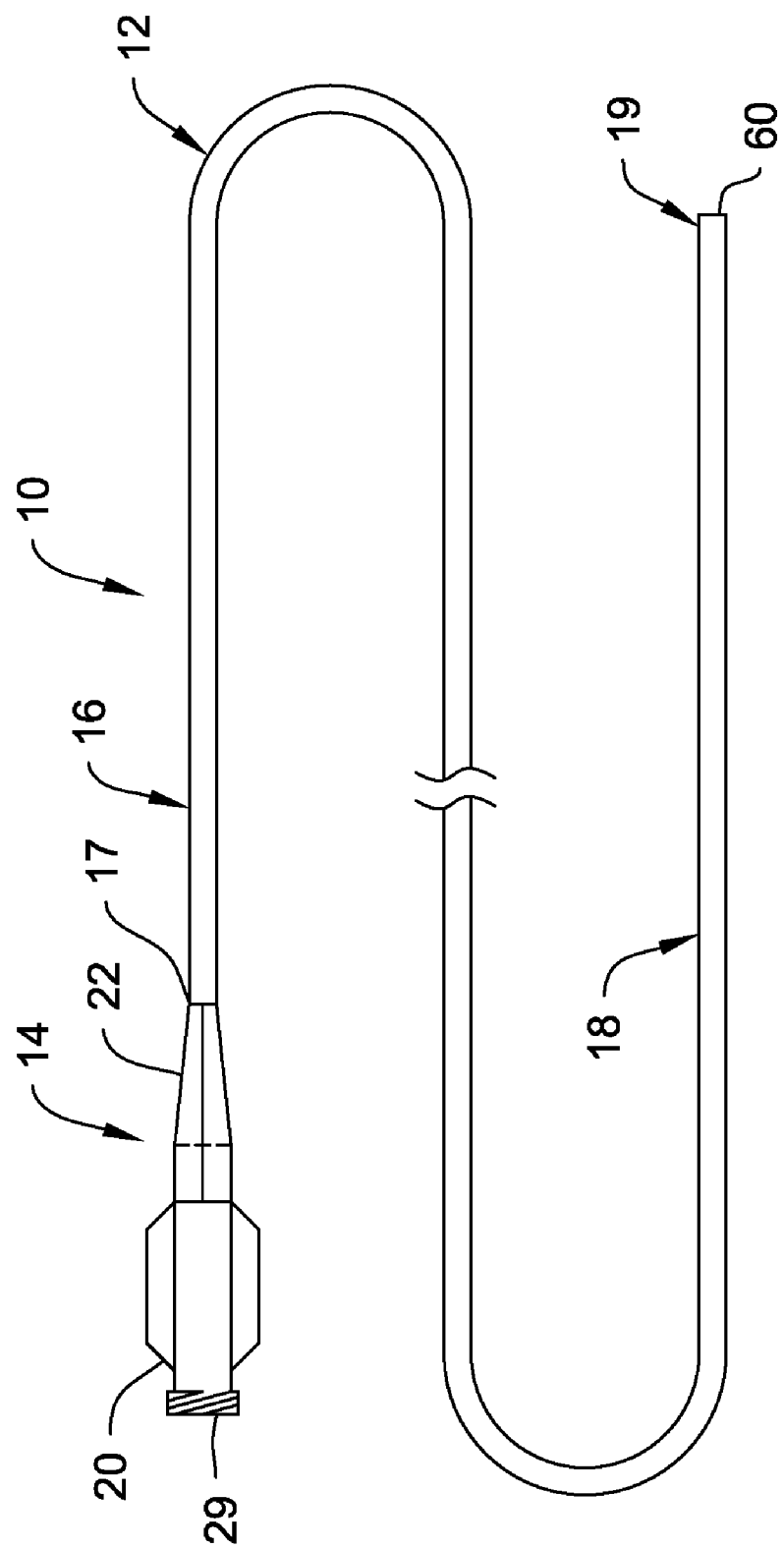
FIG. 1 is a plan view of an example catheter.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The detailed description and drawings illustrate example embodiments of the claimed invention, and are not intended to be limiting.

FIG. 1 is a plan view of an example elongated medical device, such as a guide catheter 10 or the like. Catheter 10 includes a shaft 12 having a proximal region 16, a proximal end 17, a distal region 18, and a distal end 19, and may include one or more lumen 60 extending there through. The catheter shaft 12 can be manufactured, include structure, and be made of materials so as to provide the desired characteristics of the catheter 10, depending upon the intended use. For example, the shaft 12 can be manufactured using structure and materials so as to maintain a desired level of flexibility and torquability appropriate for maneuvering the catheter 10 as desired, for example, through the vasculature of a patient. In some embodiments, the catheter 10 can include a shaft 12 that is generally characterized as having a tubular member construction that includes one or more lumen 60 extending the length of shaft 12. The one or more lumen 60 within the shaft 12 can possess an inner diameter capable of transmitting fluids, or in some cases, receiving another medical device, such as a guidewire, another catheter, for example, a diagnostic catheter, a balloon catheter, a stent delivery catheter, a distal protection device, or other device, or the like. In some embodiments, the lumen within shaft 12 can be adapted and configured to accommodate another medical device having outer diameters in the range of 5 F-10 F. As can be appreciated, the shaft 12 can include any of a wide variety of sizes, structures, layers, and/or materials that may be adapted for the particular usage intended for the catheter, some examples of which are described herein.

A hub and/or manifold structure and/or assembly 14 may be disposed adjacent proximal region 16, and as shown, is disposed on and/or about the proximal end 17 of the shaft 12. The hub assembly 14 may include a hub portion 20, and a strain relief portion 22 that may be adapted and/or configured, for example, to provide for a transition in flexibility characteristics between that of the hub 20 and the shaft 12, and may ease the transition from catheter shaft 12 to hub 20. The hub 20 may include one or more ports, such as port 29, in fluid communication with the shaft 12, and may provide for and/or define a pathway through to the lumen 60 within the shaft 12. The pathway may, for example, allow for a medical device, such as a guidewire or the like, to extend through the hub 20 into the shaft 12. Additionally and/or alternatively, the pathway may provide a path for fluid to enter the shaft 12, such as a contrast medium, medicaments, saline, an inflation fluid, or the like. In some other embodiments, for example in catheters with multiple lumens, the hub 20 may include a plurality of ports that may provide for and/or define a pathway through to the multiple lumens within the shaft 12. The hub 20 may also include an outer surface that includes structure and/or is configured to allow for gripping and/or manipulation of the hub 20. For example, the hub 20 may include structure that may aid in facilitating manipulation of the catheter 10 during navigation within the anatomy. For example, the hub 20 may include grips 30, such as wings, protrusions, widened portions having any of a wide variety or geometries, or the like, that may aid the physician in gripping and/or manipulating the hub 20 when the physician urges and/or navigates the catheter 12 by applying longitudinal and/or torsional forces to the hub 20. Those of skill in the art and others should understand that a wide variety of hub configurations may be used.

The shaft 12 can be made of a plurality of components or layers. For example, in some embodiments, the shaft 12 can have two, three, or more layers creating the tubular construction. These layers may change or be constant along the length of the shaft 12. The use of multiple different layers may allow for providing certain desirable characteristics to the shaft 12. For example, one or more of the layers can be made up of one or more tubular segments disposed on or within the shaft and made of suitable material and having suitable structure to impart the desired characteristics to portions of the shaft 12. For example, in some embodiments, an inner layer can be made of a lubricious material to allow for easy insertion of other medical devices. One or more layer may be a reinforcing layer, such as a braid, adapted to provide desirable characteristics, such as flexibility and/or stiffness characteristics to portions of the shaft 12. For another example, one or more of the layers may be made up of a plurality of tubular segments disposed along at least portions of the length of the shaft 12, each segment being made of materials having different durameters to impart varying degrees of flexibility to different sections of the shaft. The shaft 12 can be constructed using any appropriate technique, for example, by extrusion, a heat bonding and/or reflow process, heat shrink, molding, adhesive bonding, or the like, or others. Some other examples of suitable catheter shaft constructions and materials can be found in U.S. Pat. Nos. 5,569,218; 5,603,705; 5,674,208; 5,680,873; 5,733,248; 5,853,400; 5,860,963; and 5,911,715, all of which are incorporated herein by reference.

Figure 2:
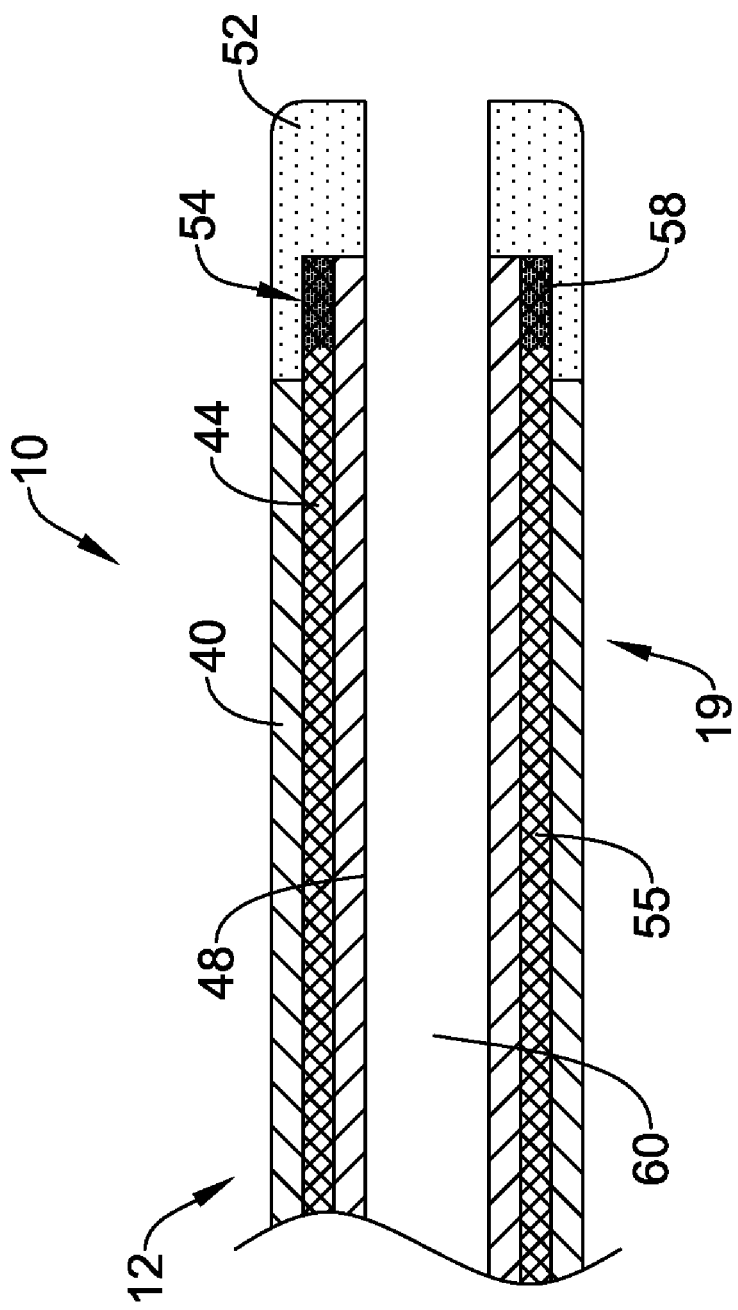
FIG. 2 is a partial longitudinal cross sectional view of the distal portion of the catheter of FIG. 1.

Referring now to FIG. 2, a longitudinal cross-sectional view of the distal portion 19 of the example shaft 12 is shown. As can be appreciated, the shaft 12 may include a braided reinforcing member or layer 44 and one or more additional members or layers in addition to the braid 44. For example, in the embodiment shown, the shaft 12 can have a three layer tubular construction including an inner tubular member or layer 48, the braided reinforcing member or layer 44 disposed about the inner tubular layer 48, and an outer tubular member or layer 40 disposed about the braid 44. The inner tubular layer 48 may define the inner lumen 60, and the outer layer 40 may define the outer surface. As may be appreciated by those of skill in the art and others, more or fewer such layers may be used in the shaft construction, as desired. For example, one or more portions of the shaft 12 may include two or more outer members and/or layers disposed about the braid 44, and/or two or more inner members or layers disposed within the braid 44. Each of the layers 40 and 48, or others, may be made of any suitable materials, for example, polymer materials, or other material, some examples of which are discussed below. And as indicated above, one or more of the layers, such as layers 40 and 48, may be made up of a single segment, or a plurality of tubular segments disposed along at least portions of the length of the shaft 12, each segment being made of materials having different durameters to impart varying degrees of flexibility to different sections of the shaft.

A distal tip member or layer 52 may be disposed at the distal end of the distal portion 19 of the shaft 12. The distal tip 52 may extend distally from the distal end of the braid 44 and/or layers 48 and 40, and may form the distal end of the shaft 12. The distal tip 52 may be made of any suitable materials, for example, polymer materials, some examples of which are discussed below. In some embodiments, the distal tip 52 can include and/or be made of a generally flexible and/or soft polymer material relative to the material of one or more of the other layers, for example, to provide a soft and/or flexible distal tip to the shaft 12. For example, the distal tip 52 may be made of a material having a softer and/or more flexible durameters to provide a soft flexible distal tip 52. However, in other embodiments, the distal tip 52 may simply be an extension of and/or may be made of the same material as one or more of the inner and/or outer tubular members or layers 40 and 48. The distal tip 52 may include a portion that overlaps with some of the other layers. For example, the braid 44 and/or the inner tubular member 48 may include portions that may extend distally such that at least a section thereof can be disposed under and/or within a portion of the distal tip 52. In other embodiments, the outer tubular member 40, or other layers or members of the shaft 12 may also include portions that may extend distally such that at least a section thereof can be disposed about and/or within a portion of the distal tip 52. In addition, while shown as a single member or layer of material, in some embodiments, the distal tip 52 may include two or more members and/or layers of material.

The braid 44 can extend the entire length of the shaft 12, or can extend through only a portion or portions of the shaft 12. Additionally, the braid 44 can end prior to the distal tip 52, can extend into a portion of the tip 52, or can extend the entire length of the tip 52. In the embodiments shown, the braid 44 extends into a portion of the distal tip 52. As can be appreciated, the braid 44 includes a distal tip section 54. The braid 44 may include and/or be made of a plurality of braid filaments 62 made of a suitable material that are braided and/or woven together in a suitable manner to create the braid 44, some examples of which will be discussed further below.

A portion of the braid 44, for example, an end portion, such as the distal tip section 54, or other portions or sections of the braid 44, can be coated with a polymeric coating material 58 that may aid in preventing and/or reducing the likelihood of the braid filaments of the braid 44 from flaring. The coating material 58 may attach, bond, and/or affix the filaments of the braid 44 together in a suitable manner to prevent and/or reduce flaring of at least the section of the braid 44 on which the coating material 58 is disposed. For example, in the embodiment shown, the coating material 58 may bond and/or affix the filaments of the braid 44 together in a suitable manner to prevent and/or reduce flaring of the distal tip section 54 of the braid 44. This may prevent and/or reduce flaring of the filaments of the braid 44 into the distal tip 52 and/or inner tubular member 48. For example, as indicated above, other layers and/or members of the shaft 12 that are disposed on, within and/or adjacent the braid 44 may be made of polymer materials, and the coating material 58 may attach, bond, and/or affix the filaments of the braid 44 together to aid in reducing and/or preventing the filaments of the braid 44 from flaring into the polymeric material of these layers during and/or after construction of the shaft 12. This may be particularly useful in maintaining end portions of a braid 44 and/or filaments of the braid from flaring. For example, the filaments in an end portion of the braid 44, such as the distal tip section 54, may have a tendency to flair outwardly and/or inwardly, for example, if the ends of the filaments are not bonded together.

In at least some embodiments, the polymer coating material 58 may have a melting point temperature that is higher than that of at least one or more, if not all, of the other polymer layers and/or materials used to construct the shaft 12. In at least some embodiments, the polymer coating material 58 may have a melting point temperature that is higher than that of the at least one of the materials used for the one or more layers disposed adjacent the coating material 58 disposed on the braid 44. For example, in the embodiment shown, the distal tip section 54 of the braid 44 can be coated with a polymeric coating material 58 that has a melting point temperature that is higher than the melting point temperature of the material of the distal tip 52 and/or the material of the inner tubular member 48, or both.

If the shaft 12 is constructed using heat bonding techniques wherein one or more of the layers and/or tip are disposed on the shaft using heat, such as an extrusion process, heat bonding process, heated molding process, heated tip bonding process, heated reflow process, or the like, such processes may be done at temperatures that are high enough to be effective, yet low enough such that they do not melt or otherwise adversely effect the polymeric coating material 58. Thus the integrity of the coating material 58 and its function in aiding in reducing and/or preventing the filaments of the braid 44 from moving relative to one another and/or flaring may be better preserved. Additionally, if a curve is imparted to the shaft 12 using a heated curving process, such a process may be done at temperatures that are high enough to be effective, yet low enough such that they do not melt or otherwise adversely effect the polymeric coating material 58—again, at least partially preserving the integrity of the coating material 58 and its function in aiding in reducing and/or preventing the filaments of the braid 44 from moving relative to one another and/or flaring.

In some embodiments, the polymer coating material 58 has a melting point temperature that is in the range of 10° F. or more higher, or in some embodiments 20° F. or more higher than the melting point temperature of at least one or more, if not all, of the other polymer layers and/or materials used to construct the shaft 12. In some embodiments, the coating material 58 has a melting point temperature that is in the range of 10° F. or more higher, or in some embodiments 20° F. or more higher than the melting point temperature of at least one of the materials used for the one or more layers disposed adjacent the coating material 58 disposed on the braid 44. For example, in some embodiments the coating material 58 has a melting point temperature that is in the range of 10° F. or more higher, or in some embodiments 20° F. or more higher than the melting point temperature of the material of the distal tip 52 and/or the material of the inner tubular member 48 and/or the material of the outer member 40, or all. In some embodiments, the melting point temperature of the polymer coating material 58 may be in the range of 400° F. or higher, while the melting point temperature of at least one or more, if not all, of the other polymer layers and/or materials used to construct the shaft 12 may be in the range of 380° F. or lower.

Figure 3:
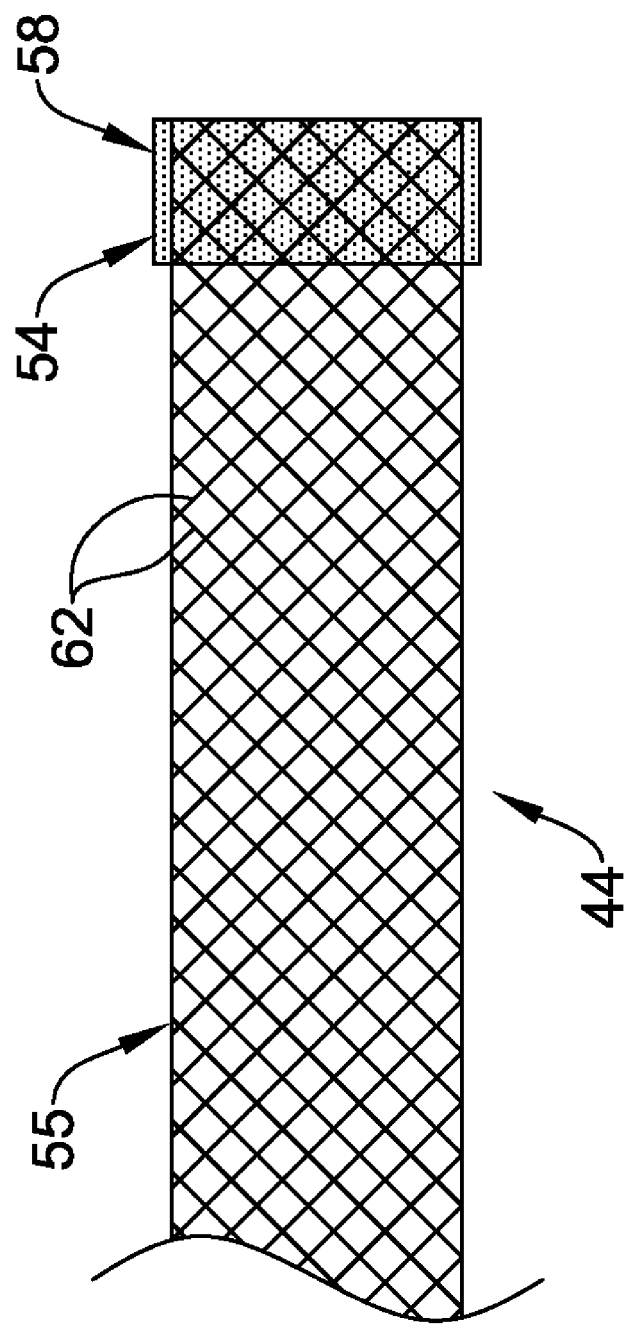
FIG. 3 is a side view of the distal portion of the braid used in the catheter of FIG. 2.
Figure 4:
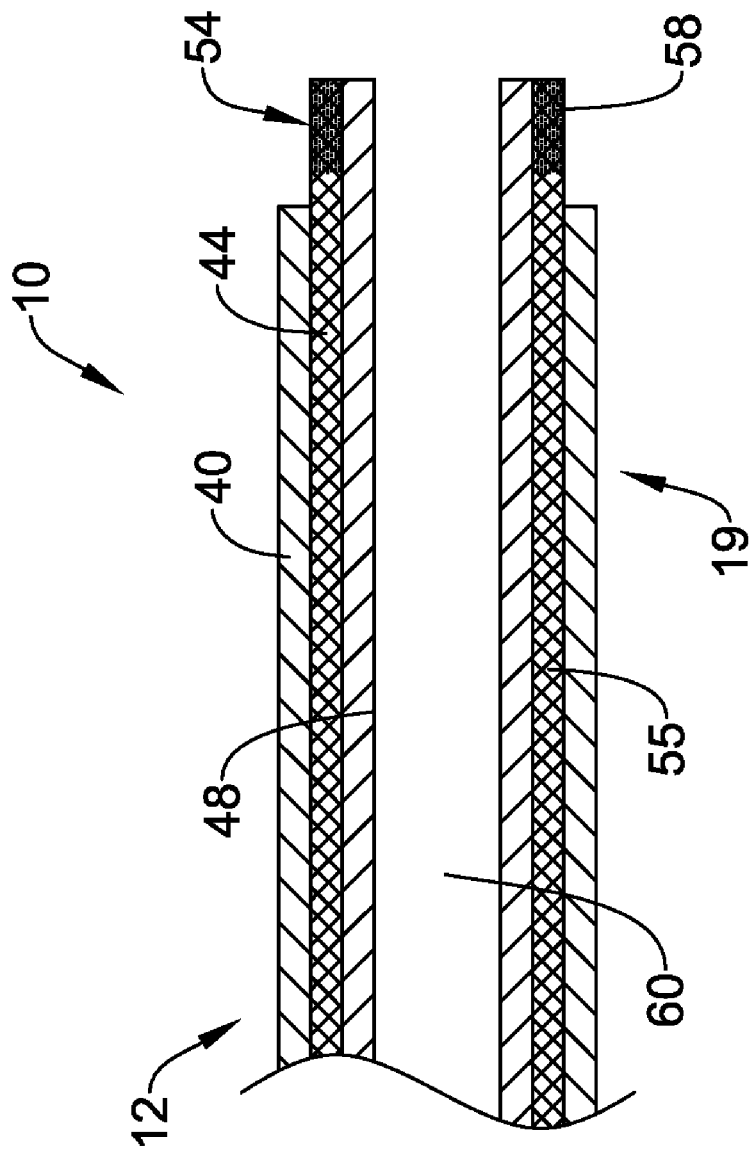
FIG. 4 a partial longitudinal cross-sectional view of the distal portion of the catheter of FIG. 2 shown prior to attachment of the distal tip.

Refer now to FIGS. 3-5 for a discussion regarding some additional discussion of some of the components of the catheter shaft 12, and some example methods of making a catheter shaft 12 that involve the use of a braid 44. FIG. 3 is a side view of the braid 44 having an outer surface 55. A portion of the braid 44, for example an end portion, such as the distal tip section 54, can be coated with a polymer coating material 58. The polymer material 58 can be applied in any known manner. In at least some embodiments, the polymer material 58 may be applied to the section 54 in a fluid and/or liquid state, and then allowed to cure. For example, a supply of the polymer material 58 can be heated to or above its melting point temperature, and applied to the distal tip section 54 and allowed to cure and/or solidify thereon. Some example methods of coating the distal tip section 54 include dip coating, spray coating, brush coating, hand coating, or the like or others. In some embodiments, the coating material 58 may be applied such that it exists only on the outer surface 55, or in other embodiments, the coating material 58 may encapsulate and/or be disposed throughout the braided material. In either case, the coating material 58 may contact and/or bond individual braid filaments 62 together.

After the section 54 is coated, and the coating material 58 is allowed to cure or solidity, the polymer material 58 may bond and/or affix the filaments of the braid 44 together in a suitable manner to prevent and/or reduce flaring of the braid 44. The section 54 may be trimmed to a desired length, and such trimming may also result in the removal of any flaring in the area that may have already occurred. The remaining section 54, however, should still include the polymer material 58 disposed thereon and/or there within to bond the filaments of the braid 44 together and thereby prevent and/or reduce the likelihood of additional flaring.

Referring now to FIG. 4, the construction of the shaft 12 may continue by the addition of other components and/or structure of the shaft 12. For example, one or more inner and/or outer layers 48/40 may be disposed and/or attached with and/or onto the braid 44 and/of shaft as desired using suitable attachment techniques, including any of those discussed herein and others. If methods using heat are used to dispose and/or attached the one or more additional polymer layers (e.g. 48/40) to the shaft 12, in some embodiments, the temperature used in such processes may be lower than that of the melting point temperature of the coating material 58. For example, such processes may be conducted at temperatures that are in the range of 10° F. or more lower, or in some embodiments 20° F. or more lower than the melting point temperature of the coating material 58.

Referring now to FIG. 5, the construction of the shaft may continue through the addition of the distal tip 52 to the distal end of the shaft 12. The material of the distal tip 52 may be disposed adjacent to and attached to the distal tip portion 54 of the braid 44. In some embodiments, a technique using heat may be used in the tip attachment process. For example, techniques such as an extrusion process, heat bonding process, heated molding process, heated tip bonding process, heated reflow process, heat shrink, or the like, may be used. If methods using heat are used to dispose and/or attached the one or more additional polymer layers (e.g. 48/40) to the shaft 12, in some embodiments, the temperature used in such processes may be lower than that of the melting point temperature of the coating material 58. For example, such processes may be conducted at temperatures that are in the range of 10° F. or more lower, or in some embodiments 20° F. or more lower than the melting point temperature of the coating material 58.

FIG. 5 illustrates the use of a heat reflow process wherein a mandrel 70 is disposed within the lumen of the shaft 12, and a tip material is disposed about the mandrel 70 and the distal end of the shaft 12. Heat is applied to melt and reflow the tip material to form the tip 52, with the tip material flowing onto the mandrel 70 such that the outer surface of the mandrel 70 may define the inner surface of the tip 52. The mandrel may then be removed, and the tip 52 may be trimmed to the desired length and/or configuration.

The catheter shaft 12 can be curved or shaped as desired utilizing appropriate shaping techniques, for example heat shaping techniques, or others. For example, catheters, such as guide catheters, can include a variety of shapes specific for different bodily passages and procedures. The stabilization of a catheter's position within a patient's anatomy is often achieved through curves or bends imparted into shaft 12. These preformed curves act by anchoring a selected portion of shaft 12 against an opposing wall within a patient's vasculature or other body portion. Proper anchoring is often achieved by matching the predisposed shape of the curved shaft 12 with the general curved anatomical shape around a targeted site. In vascular procedures involving treatment to one of the coronary arteries, often a curve is imparted proximate the distal portion of shaft 12 with the intention of placing the catheter's distal tip at a desired angle. In embodiments of catheter 10 that are designed for a procedure in a coronary artery, for example, shaft 12 can be shaped so that when it is inserted through the aorta of the patient, the curvature of shaft 12 will place distal tip at an angle that engages one of the coronary ostia. Those of skill in the art recognize some different shapes by names such as Judkins Right, Judkins Left, Amplatz Right, Amplatz Left, Bentson, Shepherd Hook, Cobra, Headhunter, Sidewinder, Newton, Sones and others, each formed in a different shape. In at least some embodiments, if a heat shaping technique is used to provide the shaft 12 with a desired shape, the temperature used in such processes may be lower than that of the melting point temperature of the coating material 58. For example, such processes may be conducted at temperatures that are in the range of 10° F. or more lower, or in some embodiments 20° F. or more lower than the melting point temperature of the coating material 58.

The layers of the shaft 12, for example, the inner tubular layer 48, the outer tubular layer 40, and/or the tip 52 can be made of and/or include any suitable material to impart the desired characteristics. Additionally, the coating material 58 can be made of and/or include any suitable material to impart the desired characteristics, with the understanding that the material may include a suitable melting point temperature, as discussed above. Examples of some suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, metals, polymer/metal composites, etc., or mixtures, blends or combinations thereof.

One example of a suitable polyether block ester is available under the trade name ARNITEL®, and one suitable example of a polyether block amide (PEBA) is available under the trade name PEBAX®, from ATOMCHEM POLYMERS, Birdsboro, Pa. One example of a suitable polyoxymethylene (POM) is Delrin™ commercially available from Dow Chemicals. Some particular examples of suitable material for use as the coating material 58 include Arnitel PL380 and Arnitel PM381, which both have a melting point temperature of about 414° F.

In some embodiments, the inner tubular layer 48 can be made of a lubricious material, for example tetrafluoroethylene (PTFE), or a copolymer of tetrafluoroethylene with perfluoroalkyl vinyl ether (PFA) (more specifically, perfluoropropyl vinyl ether or perfluoromethyl vinyl ether), or the like.

As mentioned above, the outer layer 40 or layers can be made up of one or more outer tubular segments disposed over the reinforcing layer 44, and can be constructed with any suitable materials and structures to impart the desired characteristics to the shaft 12. For example, the outer layer 40 can be made up of a plurality of outer tubular segments disposed along the shaft 12, each segment being made of materials having different durameters to impart varying degrees of flexibility to different sections of the shaft. The outer layer(s) 40 can comprise any of the materials listed above, and in some particular embodiments can include nylon, polyether block amide (PEBA), or a blend of the two and in some embodiments can have a durometer on the order of about 5-90 D. A portion of and/or all of the material(s) of outer layer 40 can be blended with a liquid crystal polymer (LCP). For example, the mixture can contain up to about 6% LCP. This has been found to enhance torqueability. The shaft can be constructed using any appropriate technique, for example, by extrusion, a heat bonding process, molding, and the like.

As indicated above, the braid 44 may include a plurality of braid filaments 62, and the braid 44 can be formed using any suitable technique or pattern. In some example embodiments, the patterns and techniques used can include 1 over 1, 2 over 2, 3 over 3, or the like. The braid 44 can be formed using a suitable number of strands or filaments 62. The number of strands or filaments 62 used will often depend upon the desired characteristics of the braid, and the patterns or techniques used to form the braid. In some embodiments, the number of strands used can range from 16 to 32, and in some embodiments from 8 to 32. The strands or filaments should be appropriately sized and shaped depending upon the desired characteristics of the braid and pattern used. For example, in some embodiments, the braid is made using braid filaments having a thickness in the range of about 0.00025 to about 0.00225 inches, and in some embodiments, from about 0.0015 to about 0.0020 inches. In some embodiments, the cross-sectional shape of the filaments can be circular, oval, or multisided, for example, triangular, square, rectangular, pentagonal, hexagonal, and so fourth.

The resulting braid 44 can be produced such that it is appropriately sized and shaped for use in the particular medical device into which it will be incorporated. In some embodiments, the braid may have a braid density of at least about 30 pic, and in some embodiments in the range of about 60 to about 300 pic. The braid diameter in some embodiments is in the range of about 0.00025 inches to about 0.00225 inches, and in some embodiments, in the range of about 0.0015 to about 0.005 inches. The braid length in some embodiments is in the range of about 20 inches to about 60 inches, but may be shorter or longer, depending upon the desired characteristics of the device.

The braid 44 and/or components or filaments 62 thereof may be manufactured from a number of different materials using appropriate braiding techniques. For example, braid filaments may be made of metals, metal alloys, polymers, metal-polymer composites or any other suitable materials. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

While several of the embodiments explained herein are explained in terms of a catheter, such as a guide catheter, it should be understood that these embodiments are merely illustrative. For example, the several embodiments may be applied to any of a broad variety of medical catheters or devices that may generally include a braided reinforcing member. For example, some or all embodiments may be applied to other types of medical catheters or devices, such as balloon catheters, fluid delivery or infusion catheters, stent delivery catheters, diagnostic catheters, angiographic catheters, atherectomy catheters, billiary catheters, urinary catheters, guidewires, embolic protection devices, endoscopes, occluders, dilators, introducer sheaths and the like, as well as for use in applications in the vasculature, digestive tract, soft tissues, and for other devices adapted for introduction into a body. It should be understood that such applications are not limited to medical operations on a human patient, and many of these embodiments have additional medical utility, for example, in veterinary applications or for other technologies.

It should be understood that this disclosure is, in many respects, only illustrative. Changes can be made in details, particularly in matters of shape, size, and arrangement of steps without exceeding the scope of the invention. The invention's scope is, of course, defined in the language in which the appended claims are expressed.

What is claimed is:

1. A method of making a catheter shaft, the method comprising:
providing an elongate braid including a plurality of filaments and having an end portion;
providing in a liquid state a first polymeric material having a first melting point;
applying the first polymeric material to the end portion of the braid in a liquid state;
allowing the first polymeric material to cure to a solid state on the braid and to attach at least some of the braid filaments together;
attaching to at least the end portion of the braid a second polymeric material after the first polymeric material has cured, the second polymeric material having a second melting point temperature that is lower than the first melting point temperature, wherein attaching the second polymeric material includes heating the second polymeric material to a temperature that is below the first melting point temperature such that during the attaching of the second polymeric material, the first polymeric material remains in a solid state.

2. The method of claim 1, wherein the second polymeric material comprises a distal tip member attached to the end portion of the braid.

3. The method of claim 1, wherein the second polymeric material comprises an outer tubular member disposed about at least a portion of the braid.

4. The method of claim 1, wherein the second polymeric material comprises an inner tubular member disposed within at least a portion of the braid.

5. A method of making a catheter shaft, the method comprising:
   providing an elongated tubular braid comprising a plurality of braid filaments and including a tip portion;
   coating the tip portion of the braid from a point distal to a proximal end to a distal end of the braid with a first polymeric material having a first melting point temperature to form a coated tip portion, wherein the first polymeric material connects two or more of the braid filaments together hindering them from flaring;
   attaching a layer of second polymeric material adjacent the coated tip portion through the use of an attachment technique that includes applying heat to the second polymeric material to heat it to a predetermined temperature, wherein the predetermined temperature is less than the melting point temperature of the first polymeric material.

6. The method of claim 5, wherein second polymeric material has a second melting point temperature lower than the first melting point temperature, and the predetermined temperature is as great as or greater than the second melting point temperature.

7. The method of claim 5, wherein the second polymeric material comprises a distal tip member attached to the tip portion of the braid.

8. The method of claim 5, wherein the second polymeric material comprises an outer tubular member disposed about at least a portion of the braid.

9. The method of claim 5, wherein the second polymeric material comprises an inner tubular member disposed within at least a portion of the braid.

10. A method of making a catheter shaft, the method comprising:
    providing an elongated tubular braid including a distal tip portion;
    coating the distal tip portion of the braid with a polymeric material having a first melting point temperature to form a coated tip portion;
    disposing a second polymeric material adjacent the coated tip portion, the second polymeric material having a second melting point temperature lower than the first melting point temperature;
    heating the second polymeric material to a temperature that is at or above the second melting point temperature but below the first melting point temperature to attach the second polymeric material to the coated tip portion.

11. The method of claim 10, wherein the second polymeric material comprises a distal tip member attached to the coated tip portion of the braid.

* * * * *